United States Patent
Tang

(10) Patent No.: US 9,549,948 B2
(45) Date of Patent: Jan. 24, 2017

(54) PURE NANO CALCIUM POWDER AND METHOD

(71) Applicant: Tieh-Chun Tang, Rowland Heights, CA (US)

(72) Inventor: Tieh-Chun Tang, Rowland Heights, CA (US)

( * ) Notice: Subject to any disclaimer, the term of this patent is extended or adjusted under 35 U.S.C. 154(b) by 0 days.

(21) Appl. No.: 14/544,970

(22) Filed: Mar. 7, 2015

(65) Prior Publication Data

US 2016/0151414 A1    Jun. 2, 2016

(30) Foreign Application Priority Data

Nov. 28, 2014   (CN) .......................... 2014 1 0704477

(51) Int. Cl.
*A61K 33/06* (2006.01)
*C01F 11/04* (2006.01)

(52) U.S. Cl.
CPC ............... *A61K 33/06* (2013.01); *C01F 11/04* (2013.01)

(58) Field of Classification Search
CPC ........... C01F 11/00; C01F 11/02; C01F 11/04; A61K 33/06
See application file for complete search history.

(56) References Cited

U.S. PATENT DOCUMENTS

2009/0087392 A1\* 4/2009 Tang ........................ A61K 8/19
424/52

\* cited by examiner

*Primary Examiner* — Richard M Rump
(74) *Attorney, Agent, or Firm* — Gary C. Honeycutt

(57) ABSTRACT

The invention relates to acid neutralizer technology, specifically involving a pure nano calcium powder and its preparation method, the nano calcium powder purity include the weight of the raw material: 3-7 parts pearl, 8-12 parts mother of pearl, 2-3 parts red coral, 20-30 parts oyster shell, clam shell 35-55 parts, Giant Clam 5-10 parts, pangolin shell 1-3 and 1-7 parts "ore" defined as limestone, cold water stone, and goose pipe rock. The preparation methods include cleaning, primary grinding, heat decomposition, rules grinding, nano grinding and mixing. Nano calcium pure powder of the present invention relates to the specific natural raw materials, and strict control of the nano calcium powder purity can provide human body absorption rates over 99%. The preparation method of the invention process is simple, convenient operation and control, stable quality, high yield, can be large-scale industrial production.

3 Claims, No Drawings

PURE NANO CALCIUM POWDER AND METHOD

TECHNICAL FIELD

The invention relates to acid neutralizer technology, specifically involving a pure nano calcium powder and its preparation method.

BACKGROUND

Today's lifestyle includes pollution of air, food and beverage processing; radiation exposure from TV, computers, mobile phones and other electronic devices. Such harmful exposure causes high acidity, which can lead to early aging, and chronic diseases, such as high blood pressure, diabetes and cancer.

Chemical imbalances in the human body and high acid factors are caused by:

1. Breathing air: air pollution in today's world is very big, the influence of breathing such pollution can damage human health by causing excessive fluid acidity.

2. Drinking water: the body should be 70% water, including blood and body fluids; at the same time, a man needs 8 glasses of water a day to maintain our physical fitness. However, pure water processing technology can deplete all minerals, and some of these substances help neutralize acids. When water is exposed to the air it changes from neutral pH 7.0 into slightly acidic. Drinking this water could lead to higher acid in the body. In addition, the current trend away from water, to a variety of acidic beverages, including most of the drinks in the supermarket, such as fruit juices, coffee, cola and soda, further increases the body's acidity.

3. Food: traditional growth of fruits, vegetables, meat, poultry and seafood are frequent use of compounds, such as chemical fertilizers, pesticides, antibiotics and growth hormones, particularly in the use of all kinds of food antibiotics and growth hormones, particularly in the use of all kinds of food additives in food, these items can promote the growth of plants and animals as well as to keep the beautiful appearance. But small amounts of these items remain on the surface of foods, causing the human daily intake of harmful chemicals, which makes human body acid higher and higher.

4. Detergents: few people know that 90% of the soaps and shampoos contain sodium dodecyl sulfate (SDS), lauryl sulfate (SLES), and polyether sodium sulfate (SLS), one drop of which will stay 5 days in the human tissue. These soap and shampoo cleaning function is very strong, but the acid chemicals are damaging a person's skin.

5. Radiation: our way of life includes exposure to microwaves, computers, mobile phones and other electronic radiation. In addition, some people are exposed to radiation from nuclear reactor leaks, caused by earthquakes and tsunami floods. In addition, because we hurry so much in today's society, more and more people have too much stress, which also drives acid values higher and higher.

These harmful particles cause human body chemistry high acid value imbalances, which will result in human aging ahead of time, energy, can also lead to chronic diseases, such as high blood pressure, diabetes and cancer. A simple solution to these problems is to neutralize body acids.

In recent years, more and more people realize the importance of pH balance to the human body. A healthy body should show alkaline pH values of 7.5 instead of acid. Therefore, how to balance the body pH became the latest and one of the most popular trends in today's society.

Acidic mixtures used as food additives in our daily life, detergent and germicide and disinfectant can damage the body, and also can produce dioxin pollution in the environment. Such materials are also used as a food additive used in animal husbandry, fishery and other industrial products. Sulfaguanidine and kappa number and others used for synthesis of antibacterial agent for human skin and hair care, or as drugs for humans and animals. However, from the safety of food and drugs, some of these materials should be under strict control, especially when the acid value is lower than standard values. So you need to use natural materials as raw materials for production of acid neutralizer, rather than synthetic compound neutralizer, especially for use in food, drinking water and beverages. In addition, acids found in common cleaners can enter the body through the skin.

After the change of the natural material contains a lot of calcium liquid of macromolecular acid neutralizer, shellfish and minerals, for example, after the material intake by human body can also be for water purification. Chinese patent application number 201410140698.7 includes a kind of pure natural superfine calcium powder preparation technology, including material selection, cleaning, crushing, grinding, calcination, hydrolyzed and superfine grinding etc. The following steps: (1) material: collecting quantity is greater than 30% of the raw materials, raw materials including sea creatures and ore; (2) cleaning: on the depth of raw materials in preliminary cleaning and cleaning; Adopts water polishing method, described in the preliminary cleaning step to remove the surface stains and epidermis of raw material, adopts high pressure water washing method, described in depth cleaning step to remove heavy metals and persistent silt on the surface of the raw material; (3) pieces: more cleaning after crushed into small particles of raw materials, referred to the small particle size is 10~20 mm; (4) calcination: the shredded granules with the method of temperature programmed heating calcining, in order to realize the decomposition of calcium ingredient materials for the purpose; Described temperature programmed steps include: (a) preliminary heat up to 350-1600° C., calcined 1.5-3 hours, until the raw material is heated to form cracks; (b) continue to heat up to 1000-2000° C., 1-3.5 hours, calcined until the complete decomposition of calcium carbonate; (5) grinding: after calcining materials for grinding and particle size of 20~40 microns; (6) hydrolysis, adding suitable amount of water for hydrolysis, get water virgin pulp; All landowners superfine grinding and drying, until will be watermill virgin pulp grinding particle size was 0.1~10 microns, in 240-260° C. drying temperature, from a single raw material of superfine calcium powder; was mixed: according to certain proportion to different raw material of superfine calcium powder, get different uses mixed superfine calcium powder.

The patent provides reference for the preparation of acid neutralizer, but made of superfine calcium powder particle size was only about micron level, human body of superfine powder of calcium absorption rate itself; and the patent did not open the mixture ratio of raw material, and the mixture ratio of raw material have a direct impact on the efficacy of nano calcium powder.

THE INVENTION

In order to overcome the shortcomings and the insufficiency in the existing technology, the aim of the present invention is to provide a kind of pure nano calcium powder, the nano calcium powder purity specific natural raw materials, and strictly control its proportioning, made of pure nano calcium powder can make human body the absorption rate reaches over 99%. Another purpose of the present invention is to provide a kind of preparation methods of nanometer calcium powder purity and the preparation process is simple, convenient operation and control, stable quality, high yield, can be large-scale industrial production.

The aim of the present invention by the following technical scheme: a pure nano calcium powder, including the weight of the raw materials as follows:
Pearl 3 to 7 parts
Mother of pearl 8-12 parts
Red coral 2-3 parts
Oyster shell 20-30 parts
Clam shell 35 and 55 parts
Giant Clam 5-10 parts
Pangolin shell 1-3 parts
Ore 3 to 7 parts
Optimization, including the weight of the raw materials as follows:
Pearl 4-6 parts
Mother of pearl 9-11 parts
Red coral 2.2-2.8 parts
Oyster shell 22 to 28 parts
Clam shell 40-50 parts
Giant Clam 6-9 parts
Pangolin shell 1.5 to 2.5 parts
Ore 4-6 parts
More optimization, including the weight of the raw materials as follows:
Pearl 5 parts
Mother of pearl 10 parts
Red coral 2.5 parts
Oyster shell 25 parts
Clam shell 45 parts
Giant Clam 7.5 parts
Pangolin shell 2 parts
Ore 5 parts The present invention uses more calcium carbonate raw materials, such as shellfish and ore, the raw materials are in natural form or waste material, abundant raw materials, low cost, and waste reduction can greatly reduce the burden of the environment, providing good social significance.

By using certain natural raw materials, and with strict control of its proportioning, the invention yields pure nano calcium powder, enabling the human body absorption rate of over 99%.

Optimization of "ore" includes limestone, cold water stone and goose pipe rock in the weight ratio of 1.5:1.5:1.0. The invention adopts the limestone, cold water stone and goose pipe rock used as ore distribution, and controls the weight ratio of 1.5-2.5:1-0.8-1.2, the calcium carbonate content is rich, the cost is low.

Another choice, "ore" includes stalactites, calcite and goose pipe rock to weight than 2-3.2-1.8:1 consisting of a mixture. The invention adopts the stalactites, calcite and goose pipe rock used as ore distribution, and controls the weight ratio of 2-3.2-1.8:1, the calcium carbonate content is rich, the cost is low.

A method of the preparation of nanometer calcium pure powder includes the following steps:

A. Cleaning: the selected raw materials, and adopt the way of high pressure sand remove dirt on the surface of the raw material;

B. Primary grinding: grinding materials after cleaning into 200-400 microns particles;

C. Heat decomposition: in inert gas particles after the primary grinding heat decomposition;

D. Rules grinding: grinding after heat decomposition of the particles into the rules of 30 to 50 microns particles;

E. Nanometer lapping: the rules after grinding particle grinding into 0.11 nm nano particles;

F. Mixing: mixing ratio of each raw material particles according to the weight, the obtained nano calcium powder purity.

Optimization, as described in step includes high pressure sand jet using natural sand or pieces of granite, mix 8-12% of the water, the pressure of 75-75 psi, the flow rate of 1.0-1.5 gallons per minute for raw materials for injection nozzle, injection time for 5-10 min. Jet angle changing in the process of injection, to thoroughly remove all contaminants.

The invention adopts cleaning by high pressure water blasting material surface, can quickly remove attached to the surface layer and the pollution of heavy metals, and the traditional way for 1 to 2 years of sun exposure and artificial cleaning steps, greatly shorten the processing time required, greatly improve production efficiency.

Optimization, as described in steps B and C includes between B1: freeze drying: after primary grinding of raw materials in freeze drying under −25° C. temperature.

The present invention adopts freeze-drying to reduce the heating cost, energy conservation and environmental protection. When calcium ingredient material grinding particles to 200-400 microns, the calcium component material particles will undergo a short period of time even freeze drying, if after grinding material is more than 400 microns, the composition of calcium so as a result of the shellfish body moisture did not discharge at this time, will be for a long, dry matter of calcium.

If shellfish have abandoned shells for two years, there is no need for freeze drying, adhesive on the surface of the clamshell, substances such as organic matter has elegance and liquefaction, therefore fall off naturally.

Calcium in the composition of the material in the inert gas for heating to produce alkali neutralization, the inert gas is preferably nitrogen, heating temperature and time depending on type of calcium substance as raw materials.

Optimization, as described in step C, pearl is first heated to 400-600° C. for heat decomposition of 1.5 to 2.5 hours, followed by heating to 800-1000° C. for 0.5 1.5 hour.

The mother of pearl is first heated to 800-1000° C. for heat decomposition of 4.5 to 5.5 hour, then heat up to 1700-1900° C. heating 4-5 hour;

The red coral is first heated to 1000-1200° C. for heat decomposition of 6.5 to 7.5 hour, then heat up to 1600-1800° C. heating 4.5 to 5.5 hour;

The oyster shell is first heated to 700-900° C. for heat decomposition 2 to 3 hours, then heated to 1600-1800° C. for 1-2 hours;

The clam shells are first heated to 500-700° C. for heat decomposition of 2.5 to 3.5 hours, then heated to 1700-1900° C. for 1.5 2.5 hours;

The giant clam is first heated to 600-800° C. for heat decomposition 3-4 hours, then heated to 1800-2000° C. for 1 hour;

The pangolin scales and shells are first heated to 900-1100° C. for heat decomposition 4-5 hour, then heated to 1300-1500° C. for 3 to 4 hours.

Optimization, as described in step C, the limestone is the first heated to 1200-1400° C. for decomposition 10-12 hours, then heated to 1800-2000° C. for 2-3 hours; Stalactites are first heated to 1100-1300° C. heat decomposition 9-11 hours, then heated to 1600-1800° C. for 2.5-3.5 hours.

Cold water stone is first heated to 1000-1200° C. for heat decomposition 8-10 hours, then heated to 1700-1900° C. for 1-2 hours. Calcite is first heated to 1100-1300° C. heat decomposition for 8-10 hours, then heated to 1600-1800° C. heating 1.5 2.5 hour. Goose pipe rock is first heated to 1200-1400° C. heat decomposition for 9-11 hours, then heated to 1700-1900° C. heating for 2 to 3 hours.

This invention uses heat decomposition, compared with the existing technology, heating time is short, only a few hours, so the production efficiency, reduce the labor time, reduce the product cost at the same time, to meet the growing market demand.

The invention through strict control of heating temperature and time of each raw material made of pure nano calcium powder can achieve maximum performance of acid and alkali neutralization.

This invention uses nanometer lapping, in −10° C. to 50° C. under the environment of nano grinding, in order to avoid the dust explosion accidents due to atomic friction, particle size after treatment between the 10-7-10-9. Use of nanometer lapping technology for fine particles will increase the total surface area of acid neutralizer, namely increased acid neutralizer and acid compounds molecular contact scope, therefore, to obtain a better acid neutralizing effect. Traditional crushing technology will normally contain calcium in utmost ground to 1 micron. As calcium carbonate with collagen still together, its molecules have very big pore. As a result, the molecules can contain amino acids, the body's absorption rate can only reach 30-40%. Using nanotechnology grinding calcium material, can make the diameter <1 nm, the traditional lapping technology can reduce the particle size at least 1000 times, it will destroy the connection of calcium carbonate and collagen amino acid, and the body's absorption rate can up to 99%.

The invention of calcium powder through mixing, due to the interaction between different ion and material together, in removing heavy metal effect has a better effect.

The preparation method of the invention process is simple, convenient operation and control, stable quality, high yield, can be large-scale industrial production.

Pure nano calcium powder of the present invention can be used for human body calcium, adjust the body pH, purify water quality, can be used to wash vegetables, fruits, meat and poultry, seafood, neutralize acid material such as pesticides and chemical fertilizers.

Nanometer calcium pure powder of the present invention can also be used for improvement of acidic soil, can play a role of let the land rest, and improve the land utilization, land is more suitable for crop cultivation, in turn, may raise the yield of crops, more safety, high quality food for humans. Beneficial effects of the present invention is that the present invention contains calcium carbonate more raw materials, such as shellfish and ore, the raw materials are natural form or as a waste material, abundant raw materials, low cost, and waste reduction can greatly reduce the burden of the environment, good social significance.

The invention by certain natural raw materials, and strictly control its proportioning, made of pure nano calcium powder can make human body the absorption rate reaches over 99%.

The invention adopts cleaning by high pressure water blasting material surface, can quickly remove attached to the surface layer and the pollution of heavy metals, and the traditional way for 1 to 2 years of sun exposure and artificial cleaning steps, greatly shorten the processing time required, greatly improve production efficiency.

The present invention adopts freeze-drying, which can reduce the heating cost, energy conservation and environmental protection.

This invention uses heat decomposition, compared with the existing technology, heating time is short, only a few hours, which improves production efficiency, reduces the labor time, reduces the product cost at the same time, to meet the growing market demand. The invention through strict control of heating temperature and time of each raw material made of pure nano calcium powder can achieve maximum performance of acid and alkali neutralization.

This invention uses nanometer lapping, at −10° C. to 50° C. under the environment of nano grinding, in order to avoid the dust explosion accidents due to atomic friction, particle size after treatment between the 10-7-10-9. Use of nanometer lapping technology for fine particles will increase the total surface area of acid neutralizer, namely increased acid neutralizer and acid compounds molecular contact scope, therefore, to obtain a better acid neutralizing effect. Traditional crushing technology will normally contain calcium in utmost ground to 1 micron. As calcium carbonate with collagen still together, its molecules have very big pore. As a result, the molecules can contain amino acids, the body's absorption rate can only reach 30-40%. Using nanotechnology grinding calcium material, can make the diameter <1 nm, whereas traditional lapping technology can reduce the particle size at least 1000 times, it will destroy the connection of calcium carbonate and collagen amino acid, and the body's absorption rate can rise to 99%.

The production of calcium powder through mixing several raw materials, due to the interaction between different ion and material together, is more effective in removing heavy metals.

For better understanding, the invention is further illustrated with test group examples. The scope of the invention is not limited to the test examples.

See Control Group 1 and Test Group 1 in Chinese application number 201410140698.7 "one kind of pure natural superfine calcium powder preparation technology of" the implementation of case 1.

EXAMPLE 1

A pure nano calcium powder is produced from a mixture of raw material as follows:
Pearl 3 parts
Mother of pearl 8 parts
Red coral 2 parts
Oyster shell 20 parts
Clam shell 35 parts
Giant Clam 5 parts
Pangolin shell 1 part
Ore 3 parts
Ore includes limestone, cold water pipe rock stone and geese to the weight ratio of 1.5:1.0.

A method for the preparation of nanometer calcium pure powder includes the following steps:

A. Cleaning: the selected raw materials are subjected to high pressure sand blasting to remove dirt from the surface of the raw materials;

B. Primary grinding: grinding materials after cleaning into 200 micron particles;

C. Heat decomposition: in inert gas particles after the primary grinding heat decomposition;

D. Rules grinding: grinding after heat decomposition of the particles into the 30 microns particles;

E. Nanometer lapping: the rules after grinding particle grinding into 0.1 nm nano particles;

F. Mixing: mixing ratio of each raw material particles according to the weight, the obtained nano calcium powder purity.

Described in step A, high-pressure sandblasting using natural sand or pieces of granite, mixed 8% of the water, the pressure for 75 psi, the velocity of 1.0 gallons per minute for raw materials for jet nozzle, the injection time for 5 min.

As described in steps B and C include steps B1: freeze drying: after primary grinding of raw materials in freeze drying under −25° C., temperature.

Described in step C, pearl is first heated to 400° C. heat decomposition 1.5 h, then heated to 800° C. heating 0.5 h;

Mother of pearl is first heated to 800° C. heat decomposition 4.5 hours, then heated to 1700° C. for 4 hours;

Red coral is first heated to 1000° C. heat decomposition for 6.5 hours, then heated to 1600° C. for 4.5 hours;

Oyster shells are first heated to 700° C. for heat decomposition 2 hours, then heated to 1600° C. for 1 hour;

Oyster shells are first heated to 500° C. for heat decomposition 2.5 h, then heated to 1700° C. for 1.5 hour;

Giant Clam is first heated to 600° C. heat decomposition 3 hour, then heated to 1800° C. heating 1 hour;

Pangolin scales and shells are first heated to 900° C. heat for 4 hours, then heated to 1300° C. for 3 hours.

When the step C raw material is limestone, first heat to 1200° C. for 10 hours decomposition, then heat to 1800° C. for 2 hours; when the raw material is cold water stone, first heat to 1000° C. for 8 hours decomposition, then heat to 1700° C. for 1 hour; when the raw material is goose pipe rock, first heat to 1200° C. decomposition for 9 hours, then heat to 1700° C. for 2 hours.

EXAMPLE 2 pure nano calcium powder, including the weight of the raw material as follows:
Pearl 4 parts
Mother of pearl 9 parts
Red coral 2.2 parts
Oyster shell 22 parts
Clam shell 40 parts
Giant Clam 6 parts
Pangolin shell 1.5 parts
Ore 4 parts
Ore is defined as limestone, cold water pipe rock stone and geese to the weight ratio of 1.7:1.0.

A method of the preparation of nanometer calcium pure powder includes the following steps:

A. Cleaning: the selected raw materials, and adopt the way of high pressure sand remove dirt on the surface of the raw material;

B. Primary grinding: grinding materials after cleaning into 250 micron particles;

C. Heat decomposition: in inert gas particles after the primary grinding heat decomposition;

D. Grinding: grinding after heat decomposition of the particles into the rules of the 35 micron particles;

E. nanometer lapping: the rules after grinding particle grinding into 0.3 nm particles;

F. mixing, mixing ratio of each raw material particles according to the weight, the obtained nano calcium powder purity.

Described in step A, high-pressure sandblasting using natural sand or pieces of granite, mixed 9% of the water, the pressure for 77 psi, the velocity of 1.1 gallons per minute for raw materials for jet nozzle, the injection time is 6 min.

As described in step B and C include steps between B1: freeze drying: after primary grinding of raw materials in freeze drying under −25° C. temperature. Described in step C, with pearl as the raw material, first heat to 450° C. heat decomposition for 1.7 hour, then heat up to 850° C. for 0.7 hour; when mother of pearl is the raw material, first heat to 850° C. for heat decomposition 4.7 hours, then heat to 1750° C. for 4.2 hours; when red coral is the raw material, first heat to 1050° C. for heat decomposition 6.7 hours, then heat to 1650° C. for 4.7 hours; when oyster shells is the raw material, first heat to 750° C. for heat decomposition 2.2 hours, then heat to 1650° C. for 1.2 hour; when clam shells is the raw material, first heat to 550° C. for heat decomposition 2.7 hours, then heat to 1750° C. for 1.7 hour; when giant clams is the raw material, first heat to 650° C. for heat decomposition 3.2 hours, then heat to 1850° C. for 1 hour; when pangolin scales and shells are the raw material, first heat to 950° C. for heat decomposition 4.2 hours, then heat to 1350° C. for 3.2 hours.

Described in step C, raw material is limestone, first to heat up to 1250° C. heat decomposition 10.5 hour, then heat up to 1850° C. heating 2.2 hour; Raw material for cold water stone, the first heat up to 1050° C. heat decomposition 8.5 hour, then heat up to 1750° C. heating 1.2 hour;

Raw materials for the goose pipe rock, the first heat up to 1250° C. heat decomposition 9.5 hour, then heat up to 1750° C. heating 2.2 hour.

EXAMPLE 3

A pure nano calcium powder, including the weight of the raw material as follows:
Pearl 5 parts
Mother of pearl 10 parts
Red coral 2.5 parts
Oyster shell 25 parts
Clam shell 45 parts
Giant Clam 7.5 parts
Pangolin shells 2 parts
Ore 5 parts
Ore is defined as limestone, cold water stone and goose pipe rock with a mixture of weight ratio of 2:1:1.

A method of the preparation of nanometer calcium pure powder includes the following steps:

A. cleaning the selected raw materials by high pressure sandblasting to remove dirt on the surface of the raw materials;

B. grinding materials after cleaning, into 300 micron particles;

C. heating the ground particles in inert gas after the primary grinding, to achieve heat decomposition;

D. rules grinding after heat decomposition of the particles into the rules of 40 micron particles;

E. nanometer lapping particles after grinding, into 0.5 nm particles;

F. mixing ratio of each raw material particles according to the weight, the obtained nano calcium powder purity.

As in step A, high-pressure sandblasting includes 10% natural sand or pieces of granite, mixed with water, a pressure of 80 psi, a flow rate of 1.3 gallons per minute for raw materials for injection nozzle, injection time for 7 min.

Steps B and C include freeze drying after primary grinding of raw materials in freeze drying under −25° C. temperature.

For processing pearl in step C, first heat up to 500° C. heat decomposition 2 hour, then heat up to 900° C. heating 1 hour;

For processing mother of pearl, first heat to 900° C. for 5 hours decomposition, and then heat to 1800° C. heating 4.5 hours;

For processing red coral, first heat to 1100° C. for 7 hours heat decomposition, and then heat up to 1700° C. for 5 hours;

For processing oyster shells, first heat to 800° C. heat decomposition for 2.5 hours, then heat to 1700° C. for 1.5 hour;

For processing clam shells, first heat to 600° C. heat decomposition for 3 hours, then heat to 1800° C. for 2 hours;

For processing Giant Clam first heat to 700° C. heat decomposition 3.5 hours, then heat to 1900° C. for 1 hour;

For processing pangolin scales and shells first heat to 1000° C. heat decomposition 4.5 hours, then heat to 1400° C. for 3.5 hours.

For processing limestone in step C, first heat to 1300° C. for 11 hours, then heat to 1900° C. for 2.5 hours;

For processing cold water stone, first heat to 1100° C. heat decomposition for 9 hours, then heat to 1800° C. for 1.5 hour;

For processing goose pipe rock, first heat to 1300° C. heat decomposition for 10 hours, then heat to 1800° C. for 2.5 hours.

EXAMPLE 4

A pure nano calcium powder, including the raw materials by weight as follows:
Pearl 6 parts
Mother of pearl 11 parts
red coral 2.8 parts
oyster shells 28 parts
Clam shell 50 parts
Giant Clam 9 parts
Pangolin shell 2.5 parts
Ore 6 parts
Ore is defined as limestone, cold water stone and goose pipe rock to the weight ratio of 2:3:1.

A method of the preparation of nanometer calcium pure powder includes the following steps:

A. cleaning: the selected raw materials are sandblasted under high pressure, to remove dirt from the surface of each raw material;

B. the primary grinding, grinding materials after cleaning into 350 microns particles;

C. heat decomposition: heat in inert gas after the primary grinding;

D. rules grinding: after the heat decomposition, the particles are reduced to 45 micron particles;

E. nanometer lapping: the rules after grinding particle grinding into 0.7 nm nano particle;

F. mixing, mixing ratio of each raw material particles according to the weight, to maintain nano calcium powder purity.

Step A is high-pressure sandblasting using natural sand or pieces of granite, mixed 11% in water, the pressure for 83 psi, the velocity of 1.4 gallons per minute for raw materials for jet nozzle, the injection time is 8 min.

As described in step B and C include steps between B1: freeze drying: after primary grinding of raw materials in freeze drying under −25° C. temperature. In step C, when the raw material is pearl, first heat to 550° C. for heat decomposition 2.3 hours, then heat to 950° C. for 1.3 hour; For processing mother of pearl, first heat to 950° C. heat decomposition for 5.3 hours, then heat to 1850° C. for 4.8 hours;

For processing the red coral, first heat to 1150° C. for heat decomposition 7.3 hours, then heat to 1750° C. for 5.3 hours;

For processing oyster shells first heat to 850° C. heat decomposition for 2.8 hours, then heat to 1750° C. heating 1.8 hour;

For processing clam shells, first heat to 650° C. heat decomposition for 3.3 hours, then heat to 1850° C. for 2.3 hours;

For processing Giant Clam, first heat to 750° C. heat decomposition for 3.8 hours, then heat to 1950° C. for 1 hour;

For processing pangolin scales and shells, first heat to 1050° C. heat decomposition for 4.8 hours, then heat to 1450° C. for 3.8 hours.

Described in step C, raw material is limestone, first heat to 1350° C. heat decomposition 11.5 hours, then heat to 1950° C. for 2.8 hours;

For processing cold water stone, first heat to 1150° C. heat decomposition 9.5 hours, then heat to 1850° C. for 1.8 hour;

For processing goose pipe rock, first heat to 1350° C. heat decomposition 10.5 hours, then heat to 1850° C. for 2.8 hours.

EXAMPLE 5

A pure nano calcium powder, including the weight of the raw material as follows:

Pearl 7 parts
Mother of pearl 12 parts
Red coral 3 parts
Oyster shell 30 parts
Clam shell 55 parts
Giant Clam 10 parts
Pangolin shells 3 parts
Ore 7 parts Ore is defined as limestone, cold water stone and goose pipe rock in the weight ratio of 2.5:1:1.2 consisting of a mixture.

A method of the preparation of nanometer calcium pure powder includes the following steps:

A. cleaning the selected raw materials, by way of high pressure sandblasting to remove dirt from the surface of the raw materials;

B. the primary grinding of raw materials, after cleaning, to obtain 400 micron particles;

C. heat decomposition: in inert gas particles after the primary grinding heat decomposition;

D. rules grinding, after heat decomposition of the particles into 50 micron particles;

E. nanometer lapping to go from 50 micron particles down to 1 nm nanoparticles;

F. mixing, mixing ratio of each raw material particles according to the weight, the obtained nano calcium powder purity.

Step A includes high-pressure sandblasting with natural sand or pieces of granite, mixed 12% of the water, the pressure for 85 psi, the velocity of 1.5 gallons per minute for raw materials for jet nozzle, the injection time for 10 min.

As described in step B and C include steps between B1: freeze drying: after primary grinding of raw materials in freeze drying under −25° C. temperature.

For processing pearl, first heat to 600° C. heat decomposition for 2.5 hours, then heat to 1000° C. for 1.5 hour;

For processing mother of pearl, first heat to 1000° C. heat decomposition for 5.5 hours, then heat to 1900° C. for 5 hours;

For processing red coral first heat to 1200° C. for decomposition 7.5 hours, then heat to 1800° C. for 5.5 hours;

For processing oyster shells first heat to 900° C. heating decomposition for 2.5 hours, and then heat up to 1800° C. for 2 hours;

For processing Clam shells, first heat to 700° C. heat decomposition for 3.5 hours, then heat up to 1900° C. for 2.5 hours;

For processing Giant Clam first heat to 800° C. heat decomposition for 4 hours, then heat to 2000° C. for 1 hour;

For processing pangolin scales and shell, first heat to 1100° C. heat decomposition 5 hours, then heat to 1500° C. for 4 hours.

For processing limestone in step C, first heat to 1400° C. heat decomposition 12 hours, then heat to 2000° C. for 3 hours;

For processing cold water stone, first heat to 1200° C. heat decomposition 10 hours, then heat to 1900° C. for 2 hours;

For processing goose pipe rock, first heat to 1400° C. for 11 hours heat decomposition, and then heat to 1900° C. for 3 hours.

EXAMPLE 6

In this example differs with the above example 1: ore is described by the stalactites, calcite and goose pipe rock to weight ratio 2:1. 2:1 consisting of a mixture.

In step C, for processing stalactites, first heat to 1100° C. heat decomposition 9 hours, then heat to 1600° C. for 2.5 hours;

For processing calcite, first heat to 1100° C. heat decomposition 8 hours, then heat to 1600° C. for 1.5 hours;

For processing goose pipe rock, first heat to 1200° C. heat decomposition 9 hours, then heat to 1700° C. for 2 hours.

EXAMPLE 7

This example and the difference is that in the above example 2: ore is described by the stalactites, calcite and goose pipe rock to the weight ratio of 2.2:1.3:1 consisting of a mixture.

For processing in step C, stalactites are first heated to 1150° C. heat decomposition 9.5 hours, then heat to 1650° C. for 2.7 hours;

For processing calcite, first heat to 1150° C. heat decomposition 8.5 hours, then heat to 1650° C. for 1.7 hours;

For processing goose pipe rock, first heat to 1250° C. heat decomposition 9.5 hours, then heat to 1750° C. for 2.2 hours.

EXAMPLE 8

In this example and the difference is that in the above example 3: ore is described by the stalactites, calcite and goose pipe rock to the weight ratio of 2.5:1.5:1 as a mixture.

In step C, stalactites are first heated to 1200° C. heat decomposition 10 hours, then heated to 1700° C. for 3 hours;

For processing calcite, first heat to 1200° C. heat decomposition 9 hours, then heat to 1700° C. for 2 hours;

For processing the goose pipe rock, first heat to 1300° C. heat decomposition for 10 hours, then heat to 1800° C. for 2.5 hours.

EXAMPLE 9

In this example and the difference is that in the above example 4: ore is described by the stalactites, calcite and goose pipe rock to the weight ratio of 2.8:1.7:1 as a mixture.

In step C, stalactites are first heated to 1250° C. heat decomposition 10.5 hours, then heated to 1750° C. for 3.3 hours;

For processing calcite, first heat to 1250° C. heat decomposition 9.5 hours, then heat to 1750° C. for 2.3 hours;

For processing the goose pipe rock, first heat to 1350° C. heat decomposition 10.5 hours, then heat to 1850° C. for 2.8 hours.

EXAMPLE 10

This example and the difference is that in the above example 5: ore is described by the stalactites, calcite and goose pipe rock to weight than 3:1.8:1 as a mixture.

In step C, for processing stalactites, first heat to 1300° C. heat decomposition 11 hours, then heat to 1800° C. for 3.5 hours;

For processing calcite, first heat to 1300° C. heat decomposition 10 hours, then heat to 1800° C. for 2.5 hours;

For processing the goose pipe rock, first heat to 1400° C. heat decomposition for 11 hours, and then heat to 1900° C. for 3 hours.

A) Removal Effect of Pesticide Residues Experiment:

(1) the test object: methamidophos, DDT, fonofos and chlordane and mirex;

(2) experimental process: the configuration of a certain concentration of pesticide solution, evenly divided into 11; Were added to the preparation of superfine calcium powder ratio 1 and implementation example 1-10 of the preparation of nano calcium powder, pure test removal effect of pesticide residues, the results are shown in table 1.

TABLE 1

| Test Item | Control Group 1 | Test Group (1) | Test Group (2) | Test Group (3) | Test Group (4) | Test Group (5) | Test Group (6) | Test Group (7) | Test Group (8) | Test Group (9) | Test Group (10) |
|---|---|---|---|---|---|---|---|---|---|---|---|
| Methamidophos elimination rate | 100% | 100% | 100% | 100% | 100% | 100% | 100% | 100% | 100% | 100% | 100% |
| DDT elimination rate | 100% | 100% | 100% | 100% | 100% | 100% | 100% | 100% | 100% | 100% | 100% |
| Fonofos elimination rate | 97% | 99% | 99% | 100% | 100% | 99% | 99% | 100% | 100% | 99% | 99% |
| Chlordane elimination rate | 100% | 100% | 100% | 100% | 100% | 100% | 100% | 100% | 100% | 100% | 100% |
| Mirex elimination rate | 97% | 100% | 100% | 100% | 100% | 99% | 99% | 100% | 100% | 100% | 100% |

Can be seen from table 1, the application of nano calcium pure powder to remove pesticide residues effect compared with contrast files of superfine calcium powder, the effect is better, especially for the removal rate of fonofos and mirex, effect is significantly enhanced relative comparative documents. This is mainly because the application of nano calcium powder purity for nanoscale, for grinding after the molecular increases the intermolecular forces make the molecules more active, the effect is better, increase the acid neutralizer and acid compounds molecular contact scope, therefore, to obtain a better acid neutralizing effect.

B. Heavy Metal Mercury Removal Experiments:

(1) the test object: mercury;

(2) experimental process: 100 mu g/L of mercury solution, divided into 11, each 500 ml; Were added to the preparation of superfine calcium powder ratio 1 and implementation example 1-10 of the preparation of nano calcium powder purity 0.25 grams, oscillation 5-10 min let stand, detection is removal rate, the results are shown in table 2.

表 2

| Test Item | Control group 1 | Test group (1) | Test group (2) | Test group (3) | Test group (4) | Test group (5) | Test group (6) | Test group (7) | Test group (8) | Test group (9) | Test group (10) |
|---|---|---|---|---|---|---|---|---|---|---|---|
| Mercury elimination rate | 84% | 94% | 95% | 96% | 95% | 95% | 94% | 95% | 96% | 96% | 95% |

Can be seen from table 1, the application of nano calcium powder purity of mercury removal rate compared with contrast files of superfine calcium powder.

C. The Bacteriostatic Effect of Experiment:
(1) the test object: the colony count in the water;
(2) the experiment process: prepare medium of 11, respectively for preparation of superfine powder and calcium ratio 1 case 1-10 of the preparation of nano calcium powder configured for the mass fraction of 0.5% pure calcium powder suspension, and spray on the culture medium, test results as shown in table 3.

| Test Item | Control group 1 | Test group (1) | Test group (2) | Test group (3) | Test group (4) | Test group (5) | Test group (6) | Test group (7) | Test group (8) | Test group (9) | Test group (10) |
|---|---|---|---|---|---|---|---|---|---|---|---|
| After 3 minutes the bacteria elimination rate. (3 min 后菌落数) (CFU/mL) | <100 | <50 | <50 | <50 | <50 | <50 | <50 | <50 | <50 | <50 | <50 |
| After 5 minutes the bacteria elimination rate (5 min 后菌落数) (CFU/mL) | 0 | 0 | 0 | 0 | 0 | 0 | 0 | 0 | 0 | 0 | 0 |

Can be seen from table 3, the application of the nanometer calcium pure powder has a more rapid sterilization effect, and time is short, lasting effect is good.

D. Clean Fruit Effect Experiment:
(1) the test object: cherry tomato
(2) experimental process: prepare cherry tomatoes two parts, one water washing, another one spraying in the above example 3 after the preparation of nano calcium powder, with clean water, taste the product, found A astringency, B no acerbity and has special sweet. This is mainly because that the shell itself is fresh material, and through this process has the bacteriostasis to the effect of acid, makes cherry tomatoes taste better.

The invention of the nano calcium powder, sprayed on fruits and vegetables can enhance the shelf life of products above, this is mainly formed from a natural layer of protective film, because calcium powder is more small, can form protective film, and closer and because shell has the effect of fresh, shell powder sprayed the fruit and vegetable surface can effectively lift the fruits and vegetables fresh.

| Test Item | Control group 1 | Test group (1) | Test group (2) | Test group (3) | Test group (4) | Test group (5) | Test group (6) | Test group (7) | Test group (8) | Test group (9) | Test group (10) |
|---|---|---|---|---|---|---|---|---|---|---|---|
| Human body absorption rate | 53% | 99% | 99% | 100% | 99% | 99% | 99% | 99% | 100% | 100% | 99% |

E. Of the Human Body Absorption Test
Will have on the proportion of superfine calcium powder preparation and implementation example 1 1-10 of the preparation of nano calcium powder purity for human absorption test, the results as shown in table 4.

Nanocalcium pure powder of the present invention to the specific natural raw materials, and strictly control the proportion of nano calcium powder purity can make human body the absorption rate reaches over 99%. The preparation method of the invention process is simple, convenient operation and control, stable quality, high yield, can be large-scale industrial production.

In the above example of the invention better implementation scheme, in addition to this, the present invention can also be the other way, on the premise of not out of the present invention idea any obvious replacement within the scope of protection of the present invention.

The invention claimed is:
1. A method for large scale industrial production of pure nano calcium powder from raw materials including 3-7 parts pearl, 8-12 parts mother of pearl, 2-3 parts red coral, 20-30 parts oyster shells, 35-55 parts clam shell, 5-10 parts giant clam, 1-3 parts pangolin shell, and 3-7 parts ore, where ore is defined as limestone, cold water stone, and goose pipe rock in the weight ratio of 1.5:1.5:1.0 comprising the following steps, applied separately to each of said raw materials:
   A. sand-blasting each selected raw material to remove dirt and other contaminants from the surface of the raw material;
   B. grinding each cleaned raw material into small particles of 200-400 microns;
   C. heating said particles from step B to a decomposition temperature in inert gas;
   D. then grinding said particles, after heat decomposition, to a size of 30-50 microns;
   E. nanometer lapping the resulting particles until the particle size is reduced to about one nanometer; then

F. mixing all the particles from step E for each raw material, to obtain the final pure nano calcium product.

2. A method as in claim 1 wherein step C for pearl includes first heating to 400 to 600 degrees C. for 1.5 to 2.5 hours, then heating to 800 to 1000 degrees C. for 0 5 to 1.5 hour;

step C for mother of pearl includes first heating to 800 to 1000 degrees C. for 4.5 to 5.5 hours, then heating to 1700 to 1900 degrees C. for 4-5 hours;

step C for red coral includes heating to 1000 to 1200 degrees C. for 6.5 to 7.5 hours, then heating to 1600 to 1800 degrees C. for 4.5 to 5.5 hours;

step C for oyster shells includes heating to 700-900 degrees C. for 2-3 hours, then heating to 1600-1800 degrees C. for 1-2 hours;

step C for clam shells includes heating to 500-700 degrees C. for 2.5 to 3.5 hours, then heating to 1700 to 1900 degrees C. for 1.5 to 2.5 hours;

step C for giant clam includes heating to 600-800 degrees C. for 3-4 hours, then heating to 1800-2000 degrees C. for 1 hour;

step C for pangolin shells includes first heating to 900-1100 degrees C. for 4.5 hours, then heating to 1300-1500 degrees C. for 3 to 4 hours;

step C for limestone includes first heating to 1200-1400 degrees C. for 10-12 hours, then heating to 1800-2000 degrees C. for 2-3 hours;

step C for cold water stone includes heating to 1000-1200 for 8-10 hours, then heating to 1700-1900 degrees C. for 1-2 hours;

step C for goose pipe rock includes heating to 1200-1400 degrees C. for 9-11 hours, then heating to 1700-1900 degrees C. for 2-3 hours.

3. A method as in claim 1, further including the step of freeze drying each raw material at a temperature below −25 degrees C. after primary grinding.

* * * * *